United States Patent [19]
Chen et al.

[11] Patent Number: 5,117,058
[45] Date of Patent: May 26, 1992

[54] CATIONIC AMIDE/ESTER COMPOSITIONS AS DEMULSIFIERS

[75] Inventors: Robert G. Chen, Sugar Land; Adelina J. Son, Houston, both of Tex.

[73] Assignee: Baker Hughes Incorporated, Houston, Tex.

[21] Appl. No.: 612,659

[22] Filed: Nov. 9, 1990

[51] Int. Cl.$^5$ .................. C07C 233/05; C07C 233/64
[52] U.S. Cl. ..................... 564/157; 564/152; 564/155; 564/156; 564/159; 564/160
[58] Field of Search ............... 564/157, 156, 160, 159; 252/320, 331, 333, 338, 341, 344, 357, 351, 353

[56] References Cited

U.S. PATENT DOCUMENTS

| | | | |
|---|---|---|---|
| 2,209,445 | 7/1940 | de Mering | 252/333 |
| 2,214,783 | 9/1940 | Wayne | 252/332 |
| 2,301,609 | 10/1942 | Bonnet | 252/335 |
| 2,457,634 | 12/1948 | Bond et al. | 252/338 |
| 2,499,370 | 3/1950 | De Groote | 252/331 |
| 2,552,528 | 5/1951 | De Groote | 252/331 |
| 2,552,529 | 5/1951 | De Groote | 252/331 |
| 2,552,530 | 5/1951 | De Groote | 252/344 |
| 2,552,531 | 5/1951 | De Groote | 252/344 |
| 2,552,532 | 5/1951 | De Groote | 252/331 |
| 2,552,533 | 5/1951 | De Groote | 252/331 |
| 2,552,534 | 5/1951 | De Groote | 252/344 |
| 2,557,081 | 6/1951 | De Groote et al. | 252/331 |
| 2,792,352 | 5/1957 | De Groote et al. | 252/331 |
| 2,792,353 | 5/1957 | De Groote et al. | 252/331 |
| 2,792,354 | 5/1957 | De Groote et al. | 252/331 |
| 2,792,355 | 5/1957 | De Groote et al. | 252/331 |
| 2,792,356 | 5/1957 | De Groote et al. | 252/331 |
| 2,792,357 | 5/1957 | De Groote et al. | 252/331 |
| 2,973,340 | 2/1961 | Case | 260/53 |
| 3,305,493 | 2/1967 | Emmons | 528/310 |
| 3,383,326 | 5/1968 | Seale et al. | 252/331 |
| 3,511,882 | 5/1970 | Seale et al. | 260/613 |
| 4,247,476 | 1/1981 | Haase et al. | 564/157 |
| 4,502,977 | 3/1985 | Buriks et al. | 252/340 |
| 4,551,239 | 11/1985 | Merchant et al. | 208/188 |
| 4,626,379 | 12/1986 | Buriks et al. | 252/340 |

FOREIGN PATENT DOCUMENTS

| | | |
|---|---|---|
| 0086066 | 8/1983 | European Pat. Off. |
| 0141585 | 5/1985 | European Pat. Off. |
| 0222587 | 5/1987 | European Pat. Off. |
| 2112388A | 7/1983 | United Kingdom |

Primary Examiner—Glennon H. Hollrah
Assistant Examiner—Shailendra Kumar
Attorney, Agent, or Firm—Rosenblatt & Associates

[57] ABSTRACT

Novel cationic amide compositions having the structure

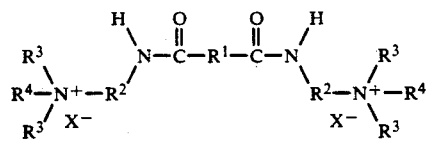

where $R^1$ represents an alkylene group of the formula $C_nH_{2n}$, and alkenyl group of the formula $C_nH_n$, or a phenyl group, or mixtures thereof, where n equals 0 to 10; $R^2$ represents $C_mH_{2m}$, where m equals 1 to 4; $R^3$ independently represents methyl, ethyl or propyl; and the combination of $R^4$ and $X^-$ represents the remnant from a quaternizing agent have been discovered and have been found useful as demulsifiers in breaking petroleum emulsions as might be produced during fireflooding petroleum recovery procedures. In one embodiment, the cationic amide/ester compositions are made by reacting (1) a dicarboxylic acid of the formula:

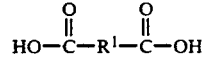

where $R^1$ represents $C_nH_{2n}$, where n equals 0 to 10, or an ester or an acid halide thereof; (2) and aminoalkylamine selected from the group consisting of dimethylaminopropylamine, dimethylaminoethylamine, diethylaminopropylamine, diethylaminoethylamine and mixtures thereof; (3) a quaternizing agent is selected from the group consisting of epichlorohydrin, dimethyl sulfate, alkyl halides and benzyl chloride; and (4) from about 0 to about 40 wt. % of at least one oxyalkylated surface active agent having HLB between about 7 and about 16.

13 Claims, No Drawings

CATIONIC AMIDE/ESTER COMPOSITIONS AS DEMULSIFIERS

FIELD OF THE INVENTION

The invention relates to the composition, preparation and use of novel cationic demulsifier compositions. More particularly, the invention relates, in one aspect, to demulsifiers for preventing, breaking or resolving emulsions of the crude petroleum emulsions, particularly petroleum emulsions derived from fireflooding.

BACKGROUND OF THE INVENTION

As crude petroleum rises from the reservoir, it passes through narrow openings, accompanied by water, gases and naturally occurring surfactants. The mixture is agitated as it is pumped up through the production tubing. Such conditions are favorable to the formation of crude petroleum emulsions. Oftentimes, wellbore solids are carried up and flushed out with the crude mixture. The wellbore solids, together with the naturally-occurring surfactants tend to stabilize the emulsions.

These petroleum emulsions cannot be processed further without first removing the major part of the water. The dehydration of petroleum emulsions is generally accomplished by techniques including, but not limited to, settling, heat treatments, centrifuging, by the application of electrical fields or by the addition of demulsifiers. Petroleum emulsions are usually too stable to be broken by the mechanical processes mentioned above. The use of chemical demulsifiers has proven more effective in resolving crude petroleum emulsions. The chemical demulsifiers exert a direct influence on the interfaces of the crude petroleum emulsions and cause a breaking or separation of the petroleum emulsions at lower temperatures and with shorter treatment times than if the demulsifiers are not used.

A large number of patents describe the preparation of chemical demulsifiers. This is largely due to the fact that petroleum emulsions vary in their compositions and characteristics depending on geographical locations. A demulsifier which works well with petroleum emulsions for one location may be ineffective in other locations.

A number of representative background patents will be mentioned briefly. De Merig revealed the use of sulfonated mineral oils as demulsifiers in U.S. Pat. No. 2,209,445. Various types of modified alkyd resins were introduced as demulsifiers in U.S. Pat. No. 2,214,783. U.S. Pat. Nos. 2,260,798 and 2,301,609 mention the use of nitrosophenol and nitrosoaromatic carboxylic acids. Blair revealed the use of alkanolamine esters in U.S. Pat. No. 2,423,563.

U.S. Pat. No. 2,457,634 discloses the use of a soap formed by the reaction of a mineral acid with a complex amine, the latter being the reaction product of formaldehyde, phenol and a non-aromatic secondary amine. U.S. Pat. Nos. 2,499,370 and 2,557,081 described processes for resolving crude petroleum emulsions which employ certain oxyalkylated phenol-aldehyde resins. Alkylene oxide condensates of various sorts are the subjects of U.S. Pat. Nos. 2,973,340; 2,552,528 through 2,552,534; 2,792,352 through 2,792,357; 3,383,326; 3,511,882; 4,502,977; 4,511,239; and 4,626,379. Also of interest as background technology in the area of alkylene oxide condensates are European Application Nos. 0,267,517; 0,147,743; 0,141,585; 0,299,348; 0,277,060; 0,264,755; 0,246,582; 0,222,587 and 0,209,850.

As noted, many emulsion breakers are very specific to certain areas and particular crude oil compositions. Most commercial emulsion breakers are formulations or blends of several chemicals. As the production field ages or more wells are put into production, new chemical or new blends may have to be put into the system.

Fireflooding is one of the thermal recovery methods. Heat is introduced into an oil reservoir through the injection of air into the reservoir and burning some of the oil in situ. By controlling the air injection and the amount of oil burned, the heat generated is kept within desired limits. The hot combustion gases generate flow toward the production wells, pushing or carrying the oil to the production zone.

Many types of demulsifiers, such as alkylene oxide condensates of various kinds and sulfonated compounds, have been applied in the field to resolve crude petroleum emulsions obtained from fireflooding with various degrees of success. For example, commodity chemical dodecylbenzenesulfonic acid (DDBSA) and its metallic salts have been used as emulsion breakers in some leases where oil is recovered through firefloods. In one lease in Canada, DDBSA was used in the system for a period of time. With age and as more wells were brought online, the emulsion characteristics changed sufficiently as to render the DDBSA ineffective.

SUMMARY OF THE INVENTION

Accordingly, it is an object of the present invention to provide a new class of compounds which will be useful as demulsifiers in breaking petroleum emulsions.

It is another object of the present invention to provide a class of cationic amide/ester demulsifiers that may be readily synthesized.

Another object of the present invention is to provide a class of demulsifiers that may be changed over the lifetime of the petroleum production to remain effective.

In carrying out these and other objects of the invention, there is provided, in one form, cationic amides having the formula:

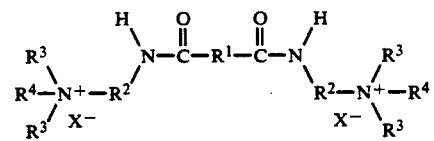

where $R^1$ represents an alkylene group of the formula $C_nH_{2n}$, an alkenyl group of the formula $C_nH_n$, or a phenyl group, or mixtures thereof, where n equals 0 to 10; $R^2$ represents $C_mH_{2m}$, where m equals 1 to 4; $R^3$ independently represents methyl, ethyl or propyl; and the combination of $R^4$ and X—represents the remnant from a quaternizing agent.

Cationic monomeric compositions of this invention may be reaction products of a dicarboxylic acid or an ester or an acid halide thereof; an aminoalkylamine and a quaternizing agent. The resulting cationic monomeric compositions may be termed amides, amide/esters or mixtures thereof.

DETAILED DESCRIPTION OF THE INVENTION

It has been discovered that amides/esters of the above compositions have utility as demulsifiers in petroleum emulsions. In another embodiment, the cationic amide/ester compositions of the invention may be described as the reaction product of (a) a dicarboxylic acid of the formula:

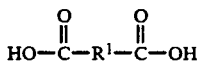

where $R^1$ represents $C_nH_{2n}$, where n equals 0 to 10 or an ester thereof; (b) an aminoalkylamine selected from the group consisting of dimethylaminopropylamine (DMAPA), dimethylaminoethylamine (DMAEA), diethylaminopropylamine (DEAPA), diethylaminoethylamine (DEAEA) and mixtures thereof; (c) a quaternizing agent selected from the group consisting of epichlorohydrin, dimethyl sulfate, alkyl halides and benzyl chloride; and (d) from about 0 to about 40 wt. % of at least one oxyalkylated surface active agent having HLB between about 7 and about 16.

In general, the amide/ester demulsifiers are made by first condensing the dicarboxylic acid or an ester thereof with the amine, followed by quaternization with the quaternizing agent. Epichlorohydrin is the preferred quaternizing agent, although other known agents may be used, such as dimethyl sulfate, alkyl halides and benzyl chloride, to list a few non-limiting examples. The resultant amide/ester materials may be used by themselves or optionally reacted or blended with an oxyalkylated surface active agent having a hydrophile/lipophile balance (HLB) between about 7 to about 16, as will be more fully described below.

As noted, a dicarboxylic acid of the formula:

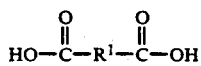

where $R^1$ represents an alkylene group of $C_nH_{2n}$, and alkenyl group of $C_nH_n$ or a phenyl group, and combinations thereof where n equals 2 to 10, is a preferred reactant. Suitable dicarboxylic acids include, but are not necessarily limited to, fumaric acid; malonic acid; succinic acid; adipic acid; suberic acid; sebacic acid; and 1,10-decanedicarboxylic acid, among others. If an ester of one of these acids is used, then an amide/ester rather than an amide, is formed. As will be seen, materials made with monocarboxylic acids do not perform well. In turn, suitable aminoalkylamines include, but are not necessarily limited to, dimethylaminopropylamine (DMAPA), dimethylaminoethylamine (DMAEA), diethylaminopropylamine (DEAPA), diethylaminoethylamine (DEAEA) and mixtures thereof.

More particularly, the process for making the novel amides/esters of the present invention involves the formation of a bis-amide through the condensation of a carboxylic acid and an N,N-di-substituted aminoalkylamine. Bis-amides are generally formed at 90°-220° C., depending on the carboxylic acid and amine used. Catalysts such as mineral acids, organic acids, alkali metals, alkali metal hydroxides or alkoxides, alkali metal amides, boric acid, $Al_2O_3$, or Ti or Zn alkoxides are used in the amidation. In one embodiment, base catalysts are preferred. The reaction times and temperature for the formation of bis-amides varies depending on the reactant carboxylic acid and amine, but will be described in a little more detail, below. The catalyst is usually left in the reaction product when they are used as demulsifiers.

U.S. Pat. No. 3,253,006 teaches that the reaction time for the formation of amides may be considerably reduced by first converting the acids to their methyl esters or other esters and their reaction with amines at high temperature (220° C.) and pressure (1800 psi). Acid halides, such as acid chlorides, of the corresponding dicarboxylic acids may also be used.

The generalized reaction route may be outlined as follows:

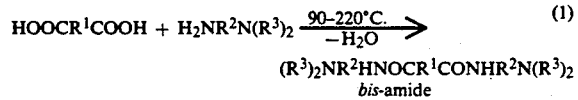

where $R^1 = C_nH_{2n}$ and n = 0 to 10; $R^2 = CH_2$, $C_2H_4$ or $C_3H_6$; and $R^3 = CH_3$ or $C_2H_5$. The bis-amides are subsequently quaternized with epichlorohydrin, as in the following reaction, presented as an example only:

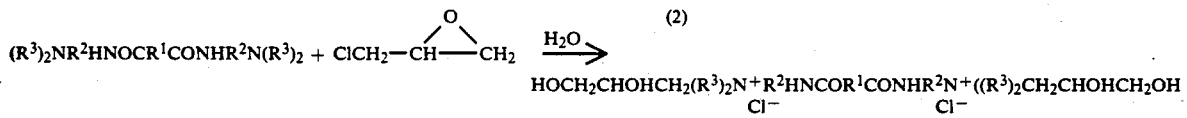

In the method of the present invention, it is preferred that the reaction be conducted at ambient or atmospheric pressures which is unusual, although it would be anticipated that the reaction could be run at higher pressures. Preferably, the materials of this invention are reacted at temperatures in the range of about 130°-220° C., and in one embodiment in a preferred range of from about 150°-165° C.

As noted, oxyalkylated surface-active agents may be used in this invention to modify the surface activity of the quaternary ammonium salts. Suitable surfactants that could be used to prepare the composition of this invention include, but are not necessarily limited to, alkoxylated alkylphenols, oxyalkylated alkylphenol/formaldehyde resins, oxyalkylated amines, oxyalkylated fatty amines, alkoxylated fatty esters, alkoxylated sorbitan esters, alkoxylated sorbitol esters, alkoxylated fatty acids, alkoxylated alkyl esters, oxyalkylated alcohols, and alkoxylated triglycerides. The preferred hydrophile/lipophile balance (HLB) values for these surfactants should generally range from about 7 to about 16, preferably from about 8 and 13. In one embodiment of the invention, the HLB values are preferred to fall within the range from about 10 to about 13.

The hydroxyl-containing surfactants may be blended with the epichlorohydrin-quaternized bis-amides (as of Equation 2) or incorporated into the reaction mixture of a dicarboxylic acid and an N,N-disubstituted aminoalkylamine at elevated temperatures to form esters and amides, followed by quaternization with epichlorohydrin, or other agent.

The invention herein will be illustrated by the following examples, which are not intended to limit the spirit or scope of the invention, but rather to be exemplary of the invention.

EXAMPLE 1

The condensate of fumaric acid and dimethylaminopropylamine was prepared by reacting 46 grams of fumaric acid and 81.4 grams of dimethylaminopropylamine at 150°-160° C. for 2 hours, followed by reaction at 200° C. for 2 hours. After cooling to 100° C., 171 grams of water were charged into the condensate and the solution continued to cool to 60° C. Quaternization was done by the addition of 73.8 g. of epichlorohydrin at 60°-100° C. over a 2-hr. period. As in all of the examples, the pressure was ambient. It was confirmed by IR, NMR, total amine and total acid analysis that the expected structure was obtained in 90% conversion.

EXAMPLE 2

The condensate of succinic acid and dimethylaminopropylamine was prepared by a reaction of 47 g. of succinic acid and 81.4 g. of dimethylaminopropylamine at 135°-150° C. for 2 hours, followed by reaction at 210° C. for 2 hours. After cooling to 110° C., 80 g. of water were charged into the condensate and the solution continued to cool to 60° C. Quaternization was effected with the addition of 73.8 g. of epichlorohydrin at temperatures of 60°-100° C. for 2 hours.

EXAMPLE 3

The condensate of adipic acid and dimethylaminopropylamine was prepared by reacting 59.6 g. of adipic acid and 81.4 g. of dimethylaminopropylamine at 135°-150° C. for 4 hours, followed by reaction at 210° C. for 2 hours. After cooling to 110° C., 134.6 g. of water were added and the solution was allowed to cool to 60° C. Quaternization proceeded with the addition of 73.8 g. of epichlorohydrin at 60°-100° C. for 2 hours.

EXAMPLE 4

The condensate of suberic acid and dimethylaminopropylamine was prepared by reacting 68.2 g. of suberic acid and 82.4 g. of dimethylaminopropylamine at 140°-155° C. for 3 hours, followed by reaction at 170° C. for 3 hours and 210° C. for one hour. The reaction mixture was cooled to 110° C. and 95 g. of water were added. The temperature was allowed to cool to 60° C. before quaternization with 74 g. of epichlorohydrin at 60°-100° C. for two hours.

EXAMPLE 5

The condensate of sebacic acid and dimethylaminopropylamine was prepared by reacting 80.9 g. of sebacic acid and 81.6 g. of dimethylaminopropylamine at 140°-158° C. for two hours, followed by reaction at 170° C. for three hours and 210° C. for one hour. After cooling to 100° C., 99.0 g. of water were added and the reaction temperature allowed to cool to 60° C. Quaternization proceeded with the addition of 74.0 g. of epichlorohydrin at 60°-100° C. for two hours.

EXAMPLE 6

The condensate of 1,10-decanedicarboxylic acid and dimethylaminopropylamine was prepared by reacting 92.0 g. of 1,10-decanedicarboxylic acid and 81.6 g. of dimethylaminopropylamine at 145°-160° C. for four hours, followed by reaction at 170° C. for two hours and 210° C. for one hour. After cooling the reaction mixture to 100° C., 103 g. of water were added and further cooling to 60° C. occurred. Quaternization proceeded with the addition of 74.0 g. of epichlorohydrin at 60°-100° C. for two hours.

EXAMPLE 7

The condensate of lauric acid and dimethylaminopropylamine was prepared by reacting 120.2 g. of lauric acid and 61.2 g. of dimethylaminopropylamine at 145°-170° C. for five hours, followed by reaction at 210° C. for one hour. After cooling to 100° C., 104 g. of methanol were added and the temperature was allowed to drop to 60° C. Quaternization with epichlorohydrin proceeded at 75° C. for five hours.

EXAMPLE 8

The condensate of oleic acid (fatty acid) and dimethylaminopropylamine was prepared by reacting 141.0 g. of oleic acid and 51.0 g. of dimethylaminopropylamine at 140°-170° C. for six hours, followed by reaction of 210° C. for one hour. After cooling to 80° C., 140 g. of methanol were added and the temperature was cooled to 60° C. A quaternization reaction with epichlorohydrin proceeded at 80° C. for three hours.

EXAMPLE 9

The condensate of adipic acid, dimethylaminopropylamine and ethoxylated nonylphenol (8 moles ethylene oxide, HLB=12) was prepared by reacting 73 g. of adipic acid, 97 g. of dimethylaminopropylamine, 28.6 g. of ethoxylated nonylphenol (8EO) and 0.8 g. of sodium methoxide for 2 hours at 150° C. and for 8 hours at 165° C. The reaction mixture was cooled to 110° C. and 47 g. of water were added. The solution was cooled to 70° C. and quaternized with 90 g. of epichlorohydrin at 70°-100° C. for 2 hours. Finally the mixture was diluted with 45 g. of methanol.

EXAMPLE 10

The condensate of adipic acid, dimethylaminopropylamine and ethoxylated tallow amine (8 mole ethylene oxide, HLB=11.4) was prepared by reacting 73 g. of adipic acid, 97 g. of dimethylaminopropylamine, 15.5 g. of ethoxylated tallow amine (8EO) and 0.8 g. of sodium methoxide at 150° C. for 2 hours, followed by reaction at 165° C. for 8 hours. The mixture was cooled to 110° C. and 47 g. of water were added. The mixture was further cooled to 70° C. and quaternized with 91.5 g. of epichlorohydrin at 70°-110° C. for 2 hours. Finally, 47 g. of methanol were added.

EXAMPLE 11

The condensate of adipic acid, dimethylaminopropylamine and polyoxyethylene (20EO) sorbitan monooleate (HLB=11.0) was prepared by reacting 73 g. of adipic acid, 97 g. of dimethylaminopropylamine, 32.5 g. of polyoxyethylene (20) sorbitan monooleate and 0.8 g. of sodium methoxide at 150° C. for 3 hours followed by reaction at 165° C. for 6 hours. The mixture was cooled to 100° C. and 49 g. of water were added. The solution was cooled to 70° C. and the amide quaternized by addition of 45 g. of epichlorohydrin over 2 hours at 70°-110° C. Finally, 49 g. of methanol were added to the mixture.

DEMULSIFICATION TESTS

Demulsification tests were conducted at a major oil company lease near Swift Current, Saskatchewan, Canada. The lease is the largest oil field in North America utilizing the fireflooding enhanced oil recovery method to produce heavy crude petroleum.

Crude petroleum emulsions were obtained directly from the well headers on location. Thus, oxidation and aging of the crude petroleum emulsions were avoided. Demulsifier samples used in these tests were diluted with 30%, by weight, water and 25%, by weight, methanol. The chemicals were injected using a microliter syringe to give the desired concentration of additive into glass testing bottles containing 100 ml of the fresh crude petroleum emulsions. Typically, 52 ml unresolved emulsions were present in the crude oil samples. The test bottles were rolled 80 times and heated in a water bath at 75° C. The efficiency of demulsification was measured by the extent of dehydration, which is monitored by the volume of water dropped (resolution of emulsions) over a period of time as indicated in Tables 1, 2 and 3. Thus, the greater the water drop, the better the emulsion breaking. After recording the water drop, the test bottles were given an additional 30 rolls and the water drop over a set period of time was observed and recorded as in Tables 4, 5 and 6. For comparison, other demulsifiers not of this invention were used in Table 7, which is most directly comparable in test procedure to Tables 1, 2 and 3, and in Table 8, most directly comparable to Tables 4, 5 and 6.

The effective amounts of the cationic amide/ester compositions of the invention will be determined by the practitioner by trial and error for particular petroleum emulsions. As explained, the emulsions vary from source to source, and thus a generalized teaching as to the effective proportions may not be given. However, in one embodiment of the invention, the proportion of the demulsifiers should be equal to or greater than about 0.01 wt. % (100 ppm) based on the petroleum emulsion. Generally, the more demulsifier used, the better is the separation, until and economic limit on the demulsifier cost is reached.

The data show that the quaternized amide/ester materials of the present invention are effective demulsifiers. It will be seen that amides made from monocarboxylic acids as in Example 7 (lauric acid) and Example 8 (oleic acid) do not perform well; see Tables 2 and 5.

TABLE 1

Resolution for Untreated and for Crude Petroleum Emulsions with Demulsifiers from Examples 1-3
(Treatment Level = 200 ppm, 80 Rolls at 75° C.)

| Time (min.) | Blank | Ex. 1 | Ex. 2 | Ex. 3 |
|---|---|---|---|---|
| 10 | 0 | 0 | 0 | 0 |
| 20 | 0 | 1 | 8 | 8 |
| 30 | 0 | 1 | 10 | 16 |

TABLE 2

Resolution for Untreated and for Crude Petroleum Emulsions with Demulsifiers from Examples 4-8
(Treatment Level = 200 ppm, 80 Rolls at 75° C.)

| Time (min.) | Blank | Ex. 4 | Ex. 5 | Ex. 6 | Ex. 7 | Ex. 8 |
|---|---|---|---|---|---|---|
| 10 | 1 | 1 | 2 | Trace | 0 | 0 |
| 20 | 1 | 8 | 3 | 3 | Trace | Trace |
| 30 | 2 | 19 | 6 | 9 | Trace | Trace |

TABLE 3

Resolution for Untreated and for Crude Petroleum Emulsions with Demulsifiers from Examples 9-11
(Treatment Level = 200 ppm, 80 Rolls at 75° C.)

| Time (min.) | Blank | Ex. 9 | Ex. 10 | Ex. 11 |
|---|---|---|---|---|
| 15 | 0 | 16 | 18 | Trace |
| 30 | 0 | 48 | 50 | 37 |

TABLE 4

Resolution for Untreated and for Crude Petroleum Emulsions with Demulsifiers from Examples 1-3
(Treatment Level = 200 ppm, 80 Rolls, 30 min. at 75° C. Followed by Additional 30 Rolls)

| Time (Min.) | Blank | Ex. 1 | Ex. 2 | Ex. 3 |
|---|---|---|---|---|
| 0.5 | 6 | 0 | 1 | 0 |
| 40 | 6 | 1 | 26 | 40 |

TABLE 5

Resolution for Unteated and for Crude Petroleum Emulsions with Demulsifiers from Examples 4-8
(Treatment Level = 200 ppm, 80 Rolls, 30 min. at 75° C. Followed by Additional 30 Rolls)

| Time (min.) | Blank | Ex. 4 | Ex. 5 | Ex. 6 | Ex. 7 | Ex. 8 |
|---|---|---|---|---|---|---|
| 0.5 | 8 | 24 | 10 | 23 | 0 | 0 |
| 40 | 8 | 31 | 12 | 24 | 0 | 0 |

TABLE 6

Resolution for Untreated and for Crude Petroleum Emulsions with Demulsifiers from Examples 1-3
(Treatment Level = 200 ppm, 80 Rolls, 30 min. at 75° C. Followed by Additional 30 Rolls)

| Time (min.) | Blank | Ex. 9 | Ex. 10 | Ex. 11 |
|---|---|---|---|---|
| 0.5 | 6 | 37 | 39 | 12 |
| 40 | 6 | 50 | 52 | 19 |

As noted, in contrast, the efficiency of demulsification of four representative conventional emulsion breakers were also tested. These commercial emulsion breakers are oxylalkylated resin type emulsion breakers which have been successfully used in many oil fields and are marketed by Baker Oil Testing. These samples were diluted with 45% by weight of methanol prior to testing. The samples could not be diluted like the inventive materials due to differences in solubility. The results are tabulated in Tables 7 and 8. These two tables demonstrate that these conventional oxyalkylated resin type emulsion breakers show no or very limited efficiency toward resolving the petroleum emulsions from the fire flooding. Results using the inventive demulsifiers from Example 10 are also presented for comparison and contrast. It may be seen that the inventive material gave considerably improved results over the conventional emulsion breakers.

TABLE 7

Resolution for Untreated and for Crude Petroleum
Emulsions Treated with Conventional Emulsion Breakers
(Treatment Level = 150 ppm, 80 Rolls at 75° C.)

| Time (min.) | Blank | Samples - Water Drop (ml) | | | | |
|---|---|---|---|---|---|---|
| | | A* | B* | C* | D* | 10 |
| 15 | 1 | 1 | 1 | 1 | 1 | 8 |
| 30 | 2 | 1 | 1 | 1 | 1 | 17 |

*Definitions of Samples A-D
Sample A - Mixture of 25% by weight of nonylphenol resin and 25% by weight of butyl resin reacted with 37.5% ethylene oxide and 12.5% propylene oxide.
Sample B - 59.6% by weight of nonylphenol resin oxyalkylated with 40.14% ethylene oxide.
Sample C - 50.1% by weight of butylphenol resin oxyalkylated with 49.9% by weight of propylene oxide.
Sample D - Mixture of oxyalkylated resins crosslinked with an epoxide. Epon ® 828, made by Shell Chemical Company.

TABLE 8

Resolution for Untreated and for Crude Petroleum
Emulsions Treated with Conventional Emulsion Breakers
(Treatment Level = 150 ppm, 80 Rolls, 30 min. at 75° C.
Followed by an Additional 30 Rolls)

| Time (min.) | Blank | Samples - Water Drop (ml) | | | | |
|---|---|---|---|---|---|---|
| | | A | B | C | D | 10 |
| 0.5 | 1 | 1 | 1 | 1 | 1 | 1 |
| 40 | 1 | 1 | 1 | 1 | 1 | 35 |

Many modifications may be made in the compositions and methods of the present invention without departing from its spirit and scope, which are defined only in the appended claims. For example, one skilled in the art may find

We claim:

1. Cationic monomeric amide compositions useful as demulsifiers in water-in-oil emulsions, said cationic monomeric amide compositions having the structure:

$$\begin{array}{c} H \quad\quad O \quad\quad O \quad\quad H \\ R^3 \diagdown \quad\quad \diagdown \| \quad \| \diagup \\ \quad\quad N-C-R^1-C-N \quad\quad R^3 \\ R^4-N^+-R^2 \quad\quad\quad\quad R^2-N^+-R^4 \\ R^3 \diagup X^- \quad\quad\quad\quad X^- \diagdown R^3 \end{array}$$

where $R^1$ represents an alkylene group of the formula $C_nH_{2n}$, an alkenylene group of the formula $C_nH_n$, or a phenylene group, or mixtures thereof, where n equals 0 to 10; $R^2$ represents $C_mH_{2m}$, where m equals 1 to 4; $R^3$ independently represents methyl, ethyl or propyl; and the combination of $R^4$ and X—represents the remnant from a quaternizing agent.

2. The cationic monomeric amide compositions of claim 1 where the quaternizing agent is selected from the group consisting of epichlorohydrin, dimethyl sulfate, alkyl halides and benzyl chloride.

3. Cationic monomeric amide compositions comprising the reaction product of:
a dicarboxylic acid or an ester or an acid halide thereof;
an aminoalkylamine; and
a quaternizing agent where the cationic monomeric compositions are selected from the group consisting of cationic monomeric amides; cationic monomeric amide/esters and mixtures thereof.

4. The cationic monomeric compositions of claim 3 where the dicarboxylic acid or an ester thereof has from about 2 to about 20 carbon atoms.

5. The cationic monomeric compositions of claim 3 where the aminoalkylamine is selected from the group consisting of dimethylaminopropylamine, dimethylaminoethylamine, diethylaminopropylamine, diethylaminoethylamine and mixtures thereof.

6. The cationic monomeric compositions of claim 3 where the quaternizing agent is selected from the group consisting of epichlorohydrin, dimethyl sulfate, alkyl halides and benzyl chloride.

7. The cationic monomeric compositions of claim 3 where an oxyalkylated surface active agent is present as a reactant with the compositions or as a separate component blended therewith.

8. Cationic monomeric amide compositions useful as demulsifiers in water-in-oil emulsions, said cationic monomeric compositions made by the process comprising the steps of:
reacting a dicarboxylic acid or its ester or an acid halide thereof, with an aminoalkylamine to give an intermediate; and
reacting the intermediate with a quaternizing agent where the cationic monomeric compositions are selected from the group consisting of cationic monomeric amides; cationic monomeric amide/esters and mixtures thereof.

9. The cationic monomeric compositions of claim 8 where the dicarboxylic acid or an ester thereof has from about 2 to about 20 carbon atoms.

10. The cationic monomeric compositions of claim 8 where the aminoalkylamine is selected from the group consisting of dimethylaminopropylamine, dimethylaminoethylamine, diethylaminopropylamine, diethylaminoethylamine and mixtures thereof.

11. The cationic monomeric compositions of claim 8 where the quaternizing agent is selected from the group consisting of epichlorohydrin, dimethyl sulfate, alkyl halides and benzyl chloride.

12. The cationic monomeric compositions of claim 8 where the reaction of the dicarboxylic acid with the aminoalkylamine is conducted in the presence of a basic catalyst.

13. Cationic monomeric amide compositions useful as demulsifiers in water-in-oil emulsions, said cationic monomeric compositions comprising the reaction product of
a dicarboxylic acid of the formula:

$$\begin{array}{c} O \quad\quad O \\ \| \quad\quad \| \\ HO-C-R^1-C-OH \end{array}$$

where $R^1$ represents $C_nH_{2n}$, where n equals 0 to 10, or an ester or an acid halide thereof;
an aminoalkylamine selected from the group consisting of dimethylaminopropylamine, dimethylaminoethylamine, diethylaminopropylamine, diethylaminoethylamine and mixtures thereof;
a quaternizing agent is selected from the group consisting of epichlorohydrin, dimethyl sulfate, alkyl halides and benzyl chloride; and
from about 0 to about 40 wt. % of at least one oxyalkylated surface active agent having HLB between about 7 and about 16.

* * * * *